(12) United States Patent
Besio

(10) Patent No.: US 9,399,133 B2
(45) Date of Patent: Jul. 26, 2016

(54) NON-INVASIVE AUTOMATED ELECTRICAL CONTROL SYSTEMS AND METHODS FOR MONITORING ANIMAL CONDITIONS

(71) Applicant: Rhode Island Board of Education, State of Rhode Island and Providence Plantations, Providence, RI (US)

(72) Inventor: Walter G. Besio, Kingston, RI (US)

(73) Assignee: Rhode Island Board of Education, State of Rhode Island and Providence Plantations, Providence, RI (US)

( * ) Notice: Subject to any disclaimer, the term of this patent is extended or adjusted under 35 U.S.C. 154(b) by 0 days.

(21) Appl. No.: 14/397,318

(22) PCT Filed: Apr. 26, 2013

(86) PCT No.: PCT/US2013/038483
§ 371 (c)(1),
(2) Date: Oct. 27, 2014

(87) PCT Pub. No.: WO2013/163594
PCT Pub. Date: Oct. 31, 2013

(65) Prior Publication Data
US 2015/0157859 A1 Jun. 11, 2015

Related U.S. Application Data

(60) Provisional application No. 61/639,153, filed on Apr. 27, 2012.

(51) Int. Cl.
*A61N 1/00* (2006.01)
*A61N 1/36* (2006.01)
(Continued)

(52) U.S. Cl.
CPC ........ *A61N 1/36025* (2013.01); *A61K 31/5513* (2013.01); *A61N 1/0408* (2013.01); *A61N 1/0472* (2013.01)

(58) Field of Classification Search
CPC . A61N 1/0408; A61N 1/0529; A61N 1/0531; A61N 1/36082; A61N 1/36053
See application file for complete search history.

(56) References Cited

U.S. PATENT DOCUMENTS

| 6,567,702 B1 | 5/2003 | Nekhendzy et al. |
| 2003/0195588 A1 | 10/2003 | Fischell et al. |

(Continued)

FOREIGN PATENT DOCUMENTS

| CN | 201453797 U | 5/2010 |
| WO | 9101756 A1 | 2/1991 |
| WO | 2011053869 A2 | 5/2011 |

OTHER PUBLICATIONS

International Preliminary Report on Patentability issued on Oct. 28, 2014 in connection with International Application PCT/US2013/038483, 12 pages.

Wagner et al., "Noninvasive Human Brain Stimulation", Annual Review of Biomedical Engineering, vol. 9, pp. 527-565, 2007.

(Continued)

*Primary Examiner* — Robert N Wieland
(74) *Attorney, Agent, or Firm* — Gesmer Updegrove LLP

(57) ABSTRACT

The present invention employed a method to control electrical activity in a target area of an animal's body by administering transcranial focal stimulation to the target area to adjust activity to normal levels. An advanced automated control system would first detect the abnormal electrical activity using tripolar concentric ring electrodes and then provides transcranial focal electrical stimulation to the target area using noninvasive tripolar concentric ring electrode system in a closed-loop continuous feedback. The automated control system would be adaptable to include the use of therapeutic drugs, either non-continuously or continuously, as a more comprehensive treatment of the abnormal electric activity.

52 Claims, 3 Drawing Sheets

(51) Int. Cl.
*A61N 1/04* (2006.01)
*A61K 31/5513* (2006.01)

(56) References Cited

U.S. PATENT DOCUMENTS

| | | |
|---|---|---|
| 2006/0136009 A1 | 6/2006 | Staffel et al. |
| 2007/0179557 A1 | 8/2007 | Maschino et al. |
| 2008/0249391 A1 | 10/2008 | Moxon et al. |
| 2009/0081179 A1* | 3/2009 | Kiliaan et al. ............... 424/94.1 |
| 2009/0210018 A1 | 8/2009 | Lozano |
| 2010/0278746 A1 | 11/2010 | Nguyen et al. |
| 2011/0137381 A1* | 6/2011 | Lee et al. ......................... 607/62 |
| 2011/0144716 A1* | 6/2011 | Bikson et al. .................... 607/45 |
| 2011/0150924 A1 | 6/2011 | Della Rocca et al. |
| 2013/0172774 A1* | 7/2013 | Crowder et al. ............. 600/544 |

OTHER PUBLICATIONS

Albert et al., "Deep Brain Stimulation, Vagal Nerve Stimulation and Transcranial Stimulation: An Overview of Stimulation Parameters and Neurotransmitter Release", Neuroscience and Biobehavioral Reviews, vol. 33, pp. 1042-1060, 2009.

International Search Report and Written Opinion issued on Aug. 12, 2013 in connection with International Application PCT/US2013/038483, 15 pages.

Search Report issued on Nov. 9, 2015 by the European Patent Office in connection with related European patent application No. 13782430.6, 8 pages.

Communication pursuant to Rules 161(2) and 162 EPC issued on Dec. 12, 2014 by the European Patent Office in connection with related European patent application No. 13782430.6, 3 pages.

* cited by examiner

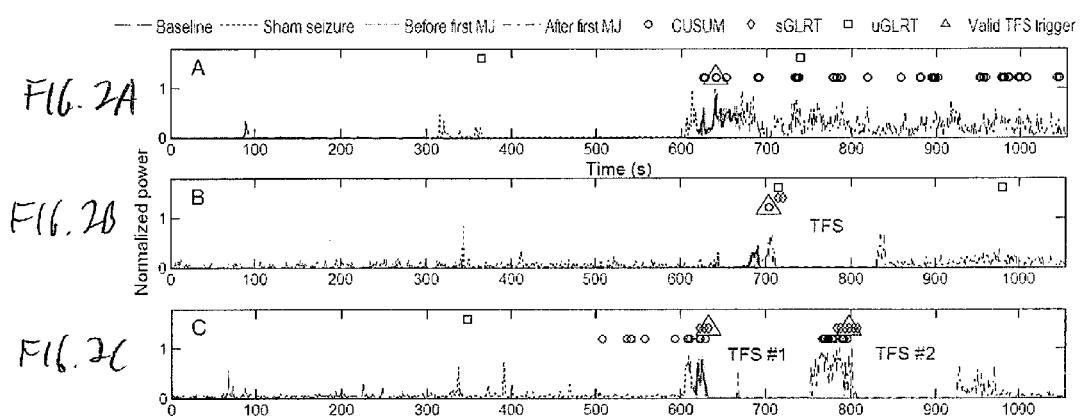

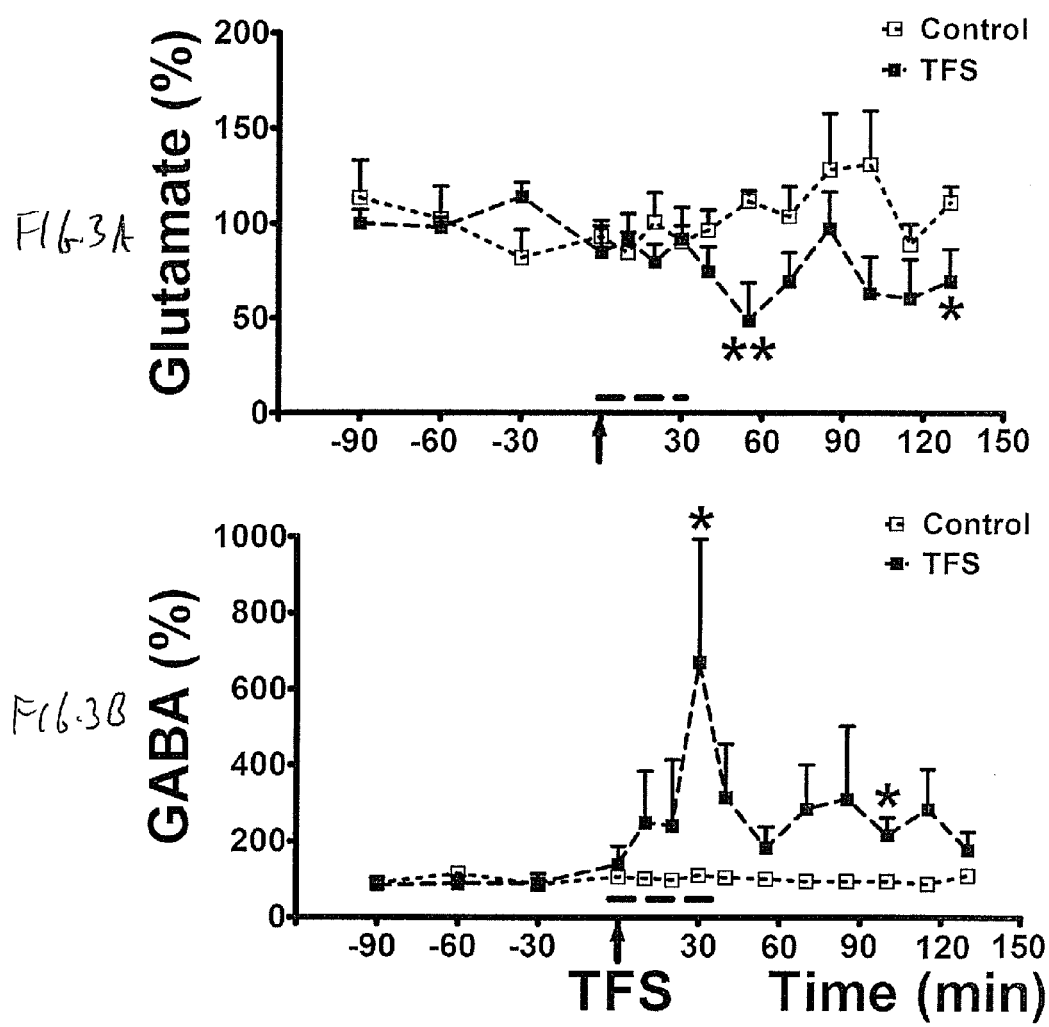

NON-INVASIVE AUTOMATED ELECTRICAL CONTROL SYSTEMS AND METHODS FOR MONITORING ANIMAL CONDITIONS

PRIORITY

Cross-Reference to Related Applications

The present invention is a U.S. National Stage filing under 35 U.S.C. 371(c) of International Application No. PCT/US13/38483 filed Apr. 26, 2013, which claims priority to U.S. Provisional Appln. No. 61/639,153 filed on Apr. 27, 2012, both of which are incorporated herein by reference in their entireties.

GOVERNMENT SPONSORSHIP

This invention was made with government support under Grant No. NS061335 awarded by the National Institute of Health. The U.S. government has certain rights to this invention.

BACKGROUND

Epilepsy is one of the most prevalent neurological disorders affecting between 1% and 2% of the world population. It is characterized by recurrent, spontaneous, and unpredictable seizures that have been associated with a chemical imbalance between excitatory and inhibitory neurotransmitters. In fact, clinical studies indicate that pharmacoresistant temporal lobe epilepsy (TLE) is related with a failure of neurtransmission mediated by glutamate and γ-aminobutyric acid. Current epileptic treatments include anti-epileptic drugs that are ineffective in up to 30% of patients and can cause significant side effects or surgery that carries significant risks and may not be effective.

Electrical stimulation of the brain has shown promise in reducing seizure frequency. Invasive techniques using implantable devices that use deep brain stimulation, the responsive neurostimulator, and the vagus nerve stimulation have been extensively used with modest success. More desirable are noninvasive forms of brain stimulation for epilepsy such as transcranial magnetic stimulation and transcranial direct current stimulation. However, these noninvasive devices suffer from being not widely accepted and to date have not shown any success in treating epilepsy.

SUMMARY

In a first aspect of the present invention, a method was invented for controlling one or more neurotransmitter levels in the brain of an animal using the release of a drug when levels were detected to be outside of the normal range. Preferably, the method used a device to monitor and detect when the level of the neurotransmitter was not within the normal range in the brain of an animals. Upon detection, one or more drugs that control neurotransmitter level in the brain were administered to the animal until the neurotransmitter levels were within the normal range in the brain. More preferably, the invention used the method in an automated system to continuously detect and effectively maintain the level of the neurotransmitters in the brain within the normal range by releasing one or more drugs.

In a second aspect of the invention, after an animal was administered one or more drugs to the control of the level of one or more neurotransmitters in the brain of an animal, if the levels of the neurotransmitters exceeded the normal range in the brain, transcranial focal stimulation was administered to adjust levels to normal levels. Preferably, an animal was administered a drug to control neurotransmitter levels either once or periodically and when the level of the neurotransmitter exceeded the normal range in the brain, transcranial focal stimulation was administered with a device that provided stimulation using a concentric electrode until the neurotransmitter level was within the normal range in the brain. More preferably, the invention used the method in an automated system to continuously detect and to maintain the level of the neurotransmitter within the normal range in the brain by administering transcranial focal stimulation.

In a third aspect of the invention, the present invention used a method to monitor and detect the level of neurotransmitter in the brain of an animal and when the level was not within the normal range of the brain either of one or more drugs was administered or transcranial focal stimulation was triggered or an effective combination of both to adjust the level of one or more neurotransmitters in the brain. Preferably, the method was used continuously to maintain the level of the neurotransmitter with the normal range in the brain.

In a fourth aspect of the invention, the present invention used a method to control one or more neurotransmitter levels in the brain of an animal by administering transcranial focal stimulation that was triggered when the level of the neurotransmitter in the brain was detected to be not within a normal range in the brain. Preferably, the level of neurotransmitter was monitored and when the level was outside of the normal range, the transcranial focal stimulation was triggered to adjust the neurotransmitter level to the normal range in the brain. More preferably, the method was an automated system performed continuously by detecting and repeating transcranial focal stimulation to maintain of the levels of the neurotransmitter within the normal range in the brain.

In a fifth aspect of the invention, the present invention used a method to control electrical activity in a target area of the body of an animal by administering transcranial focal stimulation to adjust the electrical activity to the normal range within the target area. Preferably, in this invention the electrical activity in a target area of the body was monitored using an electroencephalography device with a concentric electrode and the output of the electroencephalography device was analyzed by a cumulative sum algorithm, a generalized likelihood ratio or other algorithm or combination to detect when the electrical activity in the target area is not within normal range. When abnormal, transcranial focal stimulation was triggered and administered with a device that provided stimulation using a concentric electrode until the electrical activity in a target area of the body is within the normal range. More preferably, the method was an automated system performed continuously by detecting and repeating transcranial focal stimulation to maintain the electrical activity in a target area of the body was within the normal range. The target areas of the body for controlling the electrical activity include the brain, heart, muscle, nervous system, and other major organs or tissues having electrical activity.

In a sixth aspect of the invention, the present invention used a method to control electrical activity in a target area of the body of an animal by administering transcranial focal stimulation with one or more drugs. Preferably, in this method the drug was administered to the animal prior to, during or after administering transcranial focal stimulation to adjust the electrical activity of the target area to the normal range. More preferably, the method was an automated system performed continuously by detecting electrical activity and repeating transcranial focal stimulation and drug to maintain the electrical activity in a target area of the body is within the normal range.

In a seventh aspect of the invention, the present invention used a method for controlling an epileptic seizure in the brain of an animal using an automated seizure control system. Preferably, the method detected an epileptic seizure event when the pre-set seizure electrical activity in the brain exceeded a determined electrical activity using an electroencephalography device with a concentric electrode, and the output of the electroencephalography device was analyzed by a cumulative sum algorithm, a generalized likelihood ratio or other algorithm or combination. When the electric activity was analyzed to be an epileptic seizure, transcranial focal stimulation was triggered and administered with a device that provided stimulation using a concentric electrode until the electrical activity in the brain within the normal range or the epileptic seizure has stopped. More preferably, the method was an automated system performed continuously by monitoring and repeating transcranial focal stimulation to maintain the electrical activity in a brain within normal levels or to stop an epileptic seizure event. The method is an automated system and was used with one or more drugs to control an epileptic seizure event.

In accordance with many aspects of the invention using a electroencephalography device for detection or a device providing an transcranial focal stimulation, the concentric electrode is a concentric electrode having a center disc and one or more rings, preferably two or more rings, and more preferably two rings, referred to as tripolar. Most preferably, the concentric ring electrodes reside at a specific distance to each other as defined by the ratio between the ring and the size of the ring used, for both the electroencephalography device for detection or the device providing a transcranial focal stimulation. These procedures used one or more concentric electrodes in an electroencephalography device for detection or a device providing a transcranial focal stimulation.

BRIEF DESCRIPTION OF THE DRAWINGS

The following description may be further understood with reference to the accompanying drawings in which:

FIGS. 2A-2C show normalized tEEG power and seizure detections for CUSUM, sGLRT and uGLRT detectors: Panel A—control rat; Panel B—one dose TFS treated rat; panel C—two dose TFS treated rat.

FIGS. 3A-3B show an average glutamate and GABA levels measured in the hippocampus of rats before, during, and after TFS was applied on the skull for 30 minutes.

DETAILED DESCRIPTION

Figure 1:
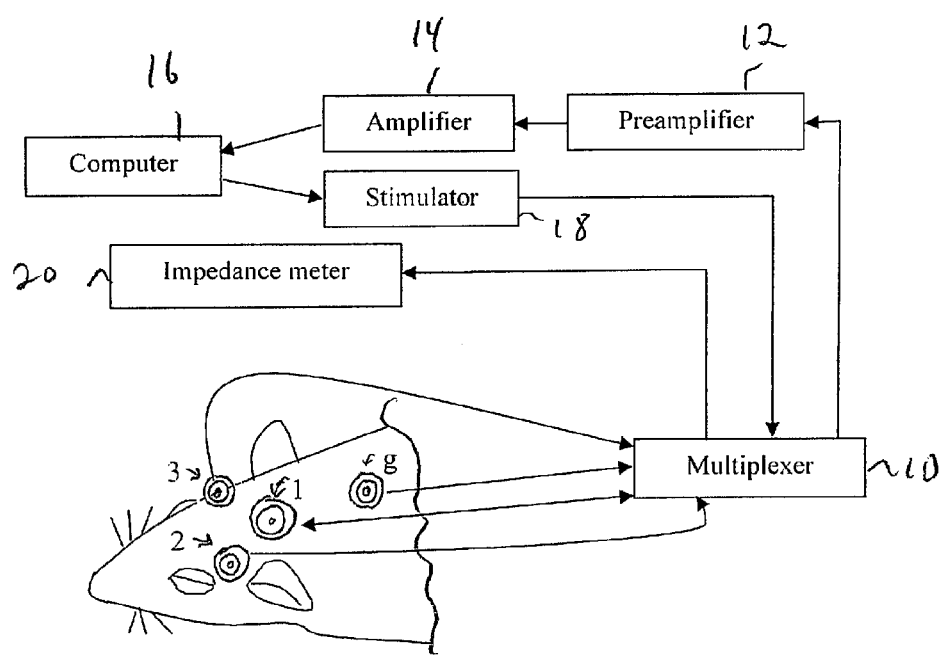
FIG. 1 shows a schematic representation of the experimental setup. The TFS was applied between the outer ring and the middle disc of electrode (1). Electrodes (1), (2), and (3) were used for recording and (g) was the ground.

The present invention provides a method of controlling electrical activity in a target area of an animal's body by administering transcranial focal stimulation to the target area to adjust activity to normal levels. An advanced automated control system first detects the abnormal electrical activity using tripolar concentric ring electrodes and then provides transcranial focal electrical stimulation to the target area using noninvasive tripolar concentric ring electrode system in a closed-loop continuous feedback. The automated control system is adaptable to include the use of therapeutic drugs, either non-continuously or continuously, as a more comprehensive treatment of the abnormal electric activity.

Examples of target areas of the body include brain, heart, and nerves corresponding to abnormal electric activity conditions of epilepsy, heart attack, or pain. For example, epilepsy affects approximately one percent of the world population. Antiepileptic drugs are ineffective in approximately 30% of patients and can have drastic side effects. The automated seizure control system was demonstrated in an animal model using pentylenetetrazole-induced seizures through single and multiple stimulations. Stimulations were automatically triggered by a real-time electrographic seizure activity detector based on a disjunctive combination of detections. An automatically triggered stimulation was able to reduce the electrographic seizure activity power in the stimulated group by 70% compared to untreated animals. In addition, the automated noninvasive transcranial focal electrical stimulation system was found to alter levels of neurotransmitters in the brain of animals that can provide for novel ways to improve the efficacy and reduce the dose of antiepileptic drugs thereby reducing the level of side effects.

Certain terms are defined herein as follows:

"Abnormal" means not within the normal range as defined by the device or level well recognized by a medical expert in the field.

"Automated" means that the device automatically applies the therapy with physiological feedback about the animal that the therapy is being applied to.

"Biopotential" means any signal that is an electric quantity, either voltage, current or field strength, caused by chemical reactions of charged ions through the transfer of information between and within cells. Voltage difference measured between points in living cells, tissues, and organisms. Ionic voltages produced as a result of the electrochemical activity of excitable cells.

"Electrography Device" means any device that can measure electrical activity from a living source that includes, but not limited to, electroencephalography (EEG), electromyography (EMG), and electrocardiography (ECG).

"Electroencephalography Device" means any device that can measure electrical activity of the brain.

"Non-invasive" means any device or instrument that does not include penetrate the integrity of the body, and specifically includes those device or instrument placed on the skin or scalp.

"Normal Range" means normal range as defined by the device or level well recognized by a medical expert in the field.

"Tripolar Concentric Ring Electrode" means any electrode consisting of three concentric rings with a distinct mathematical Laplacian relationship between ring spacing and diameter as described by Besio in the patent application, WO 2001/056626A1.

"Neurotransmitter" means any neurotransmitter that is capable of affecting neurological activity or neurons either alone or together with another neurotransmitter. Neurotransmitters include amino acids, peptides, monoamines and other neurological molecules. Amino acids include glutamate, aspartate, D-serine, γ-aminobutyric acid (GABA), and glycine. Monoamines include other biogenic amines and catecholamine such dopamine (DA), norepinephrine (noradrenaline; NE, NA), epinephrine (adrenaline), histamine, and serotonin (SE, 5-HT). Other neurological molecules include, but are not limited to, acetylcholine (ACh), adenosine, anandamide, and nitric oxide.

International Patent Application Publication No. WO 2001/056626A1 discloses a unique class of concentric electrodes that have surprising performance properties because of their unique spacing between concentric rings. The preferred array of rings for an electrode has a center disc and two rings or tripolar orientation, where the center disc has a diameter of $d_1$, the first electrical ring has a diameter of $d_2$ that is larger than $d_1$, and having the ring thickness, $t_2$, such that $4 \leq d_1/t_2 \leq 6$, and a second electrical ring has a diameter of $d_3$ that is larger than $d_2$ and having the ring thickness, $t_3$, such that $4 \leq d_1/t_3 \leq 6$. Three or more rings will have a similar relationship. These concentric ring electrodes have unique capabilities that enable them to perform the second spatial derivative, the Laplacian, on the surface potentials. Previously it was shown that tEEG, Laplacian electroencephalography (EEG) with the tripolar concentric ring electrode configuration, is superior to conventional EEG with disc electrodes because tEEG has significantly better spatial selectivity, signal-to-noise ratio, localization, approximation of the analytical Laplacian, and mutual information. These findings suggested that tEEG may be superior at detecting seizures, or other neurological disorders, to conventional EEG with disc electrodes.

Unlike electrical stimulation via conventional disc electrodes that is usually applied across the head, transcranial electrical stimulation via concentric ring electrodes has a much more uniform current density and focuses the stimulation directly below the electrodes. This form of stimulation is referred to as transcranial focal stimulation.

Transcranial focal stimulation showed promise to reduce acute seizures in a pilocarpine-induced status epilepticus model where transcranial focal stimulation via tripolar concentric ring electrodes (TCRE) attenuated electrographic seizure activity toward baseline and stopped the progression of behavioral seizures. Moreover, interruption of the seizure activity appeared to be a long-lasting effect and the transcranial focal stimulation treatment significantly enhanced the survival of rats after status epilepticus. Similarly, transcranial focal stimulation was found to significantly decrease severe myoclonic jerks induced by penicillin both in number and duration.

A third animal model was tested to more directly examine the effect of transcranial focal stimulation on brain disrupting drugs. The pentylenetetrazole model was employed, which is widely used for testing both seizure susceptibility and screening of new antiepileptic drugs. In the preliminary work, the potential of transcranial focal stimulation to reduce pathological synchronization of pentylenetetrazole-induced electrographic activity was studied. Cross-channel coherence was used to measure synchrony changes at particular frequency bands in electrographic activity recorded from tripolar concentric ring electrodes on the rat scalp. Coherence measurements were performed on tEEG segments recorded (a) during the pre-seizure stage, (b) after administration of pentylenetetrazole, and (c) immediately after application of transcranial focal stimulation. A significant increase in synchrony within the beta-gamma frequency bands during seizures was demonstrated as well as the potential of transcranial focal stimulation to significantly reduce this synchrony.

To examine the short term impact of transcranial focal stimulation via tripolar concentric ring electrodes on the scalp of rats, in pentylenetetrazole-induced seizures it was found transcranial focal stimulation caused reductions of seizure electrographic activity power for 4-min long time windows starting after the transcranial focal stimulation treatment and throughout the duration of myoclonic activity.

An important advantage of transcranial focal stimulation is that it does not cause motor contractions as is common with electroconvulsive therapy, another form of transcranial electrical stimulation. The effects of transcranial focal stimulation via tripolar concentric ring electrode on rat cortical integrity were studied. Histomorphological analysis was used to assess cortical and hippocampal areas below the transcranial focal stimulation site for neuronal damage. Control and transcranial focal stimulation treated animals were anaesthetized and transcranially perfused. The brains were removed, post-fixed, and cut into coronal sections. Slices were mounted on gelatinized slides, Nissl stained for brightfield analysis, and photographed with a microscope equipped with a digital camera. Images where digitized to grayscale and the integrated optical density was measured with densitometry software. No significant difference in integrated optical density or cell counting was found for control and TFS treated rat brains. Further, morphological analysis did not show any pyknotic neurons, cell loss or gliosis that might confirm any neuronal damage.

Detection of seizures is challenging because: (1) there is no objective definition of what constitutes seizure electrographic activity, (2) background brain activity is non-stationary, (3) the changes introduced by seizures are non-stationary, (4) movement artifacts or non-seizure activity of the brain may resemble seizure activity, and (5) early detection, with high accuracy and specificity are required.

In the present invention, feasibility is shown for an automatic seizure control system in rats with pentylenetetrazole-induced seizures through single and multiple applications of transcranial focal stimulation via tripolar concentric ring electrode. Transcranial focal stimulation was automatically triggered by real-time electrographic seizure activity detectors based on a disjunctive combination of the CUSUM algorithm and generalized likelihood ratio test (GLRT). Experiments were performed to confirm the effect of automatically triggered transcranial focal stimulation on pentylenetetrazole-induced electrographic seizure activity in rats.

Recently many studies have been performed in the field of seizure detection. In previous work, it was found that a significant increase in tEEG power corresponded to seizure onset using population grand average power spectral density estimates and frequency band analysis. These findings agree well to findings of others where power related features were used as features for seizure detection including variance in energy, signal and wavelet energy.

In the present invention, seizure onset detection methodologies proposed were based solely on detecting the changes in signal power. Until this invention, no group has been successful at employing transcranial focal stimulation using TCRE for the automated detection and control of seizures.

As an additive approach, the use of transcranial focal stimulation using TCRE was used in tandem with the detection of neuromodulator as a method of enhanced drug therapy to more safely control seizures. High frequency electrical stimulation (HFS) in hippocampus has been considered as a strategy to reduce seizure activity in patients with refractory TLE. HFS delays the epileptogenesis process and enhances the refractoriness to subsequent seizures during the postictal period in an experimental model of TLE. In lithium-pilocarpine-induced status epilepticus, subeffective doses of antiepileptic drugs that increase the neurotransmission mediated by GABA improve the anticonvulsant effects induced by HFS applied in ventral hippocampus.

Other aspects of the present invention, it is shown for the first time that non-invasive transcranial focal stimulation using TCRE was effective in modulating levels of GABA in status epilepticus induced by lithium-pilocarpine (LP) in rats receiving TFS, alone and combined with subeffective doses of diazepam, an antiepileptic drug that belongs to the group of benzodiazepines. Diazepam is currently considered the drugs of choice to stop the status epilepticus and avoid its consequences. In addition, hippocampal amino acids were released following transcranial focal stimulation in normal rats further demonstrating the potentiating effects of TFS with TCRE. These results provide a non-invasive approach to treatment of epilepsy in concert with drugs as a method to more effectively reduce epileptic episodes.

EXAMPLE 1

Development of a Seize Detecting Algorithm

A cumulative sum (CUSUM) seizure detection algorithm was developed to trigger an automatic application of transcranial focal stimulation. The CUSUM algorithm was first evaluated on pre-recorded data and detected the electrographic seizure activity in all experiments well in advance of the behavioral seizure activity.

The CUSUM is a signal change detector traditionally used in quality control, intrusion detection, spam filtering and medical systems to identify changes in probability distribution of a stochastic random process. The CUSUM was selected because it is able to rapidly and reliably detect small changes and is insensitive to the probability distribution of the data.

Although there is no optimality associated with the GLRT it has been shown to work well in practice. Moreover, asymptotically, it was shown that the GLRT is a uniformly most powerful test among tests that are invariant, i.e. among all possible invariant tests that have a given probability of false alarm it gives the highest probability of detection.

EXAMPLE 2

Signal Acquisition and Preprocessing

As shown in FIG. 1 one TCRE (diameter=1.0 cm, was used to record and stimulate and was centered on the top of the head (1). The front edge of the electrode was placed near the site that should be the bregma since we were not able to see it. Two other TCREs (diameter=0.6 cm) were placed bilaterally behind the eyes, but in front of the ears (A 2.0 mm, L 9.0 mm relative to the central electrode) on both sides of the head (2,3). An isolated ground electrode was attached on the top of the neck behind the ears (g). These particular electrode locations were chosen due to size constraints and brain anatomy of adult rats. The rat was returned to its cage and allowed food and water ad libitum for approximately 24 h until the experimental procedure began. All experiments were performed in the afternoon.

The electrodes (1, 2, 3, g) were coupled to a multiplexer 10 in communication with a preamplifier 12. The output of the preamplifier was coupled to an amplifier 14, the output of which was provided to a computer 16. The computer 16 also provided a stimulator signal to a stimulator 18, which was also in communication with the multiplexer 10 to provide time multiplexed stimulation signals to the electrodes. The multiplexer 10 was also coupled to an impedance meter 20, in part, to monitor the operation of the electrodes.

The tEEG signals were preamplified (gain 100 and 0.3 Hz high pass filter) with a custom built preamplifier and then amplified using a Grass Model NRS2 Neurological Research System with Model 15A54 AC amplifiers (Grass Technologies, West Warwick, R.I., USA) with a gain of 1000 and band pass of 1.0-100 Hz with the 60 Hz notch filter active, and digitized (16 bits, 256 Hz). Two differential signals from each electrode were combined with an algorithm to give Laplacian derivation of the signals. The algorithm is two-dimensional and weights the middle ring and central disc difference sixteen times greater than the outer ring and central disc difference.

For automatic seizure onset detection data recorded from electrode (1) was used for transcranial focal stimulation (TFS) treated rats while data from the electrode with the lowest impedance was used for the control group. This was done to ensure the highest possible quality of the tEEG signal for all the groups. For assessing the effect of TFS on electrographic seizure activity power data recorded from electrode (1) was used for both TFS treated and control groups to compensate for potential difference in power between electrodes differing in size and/or location. Such a difference is not crucial for automatic seizure onset detection due to the fact that individual detection models were used for each rat. Real-time signal acquisition and processing as well as post signal processing was performed using Matlab (Mathworks, Natick, Mass., USA).

The day of the experiment, the rats were allowed to habituate to the room and the electrode cables for approximately 30 min. First, the skin-to-electrode impedance of each electrode was measured. If the outer ring or central disc skin-to-electrode impedance for the 1.0 cm dia. electrode (1) to the isolated ground electrode (g) of FIG. 1 was less than 10 KΩ, then the rat was given TFS once or twice. If this impedance was greater than 10 K, but less than 25 KΩ and impedance for at least one of the 0.6 cm dia. electrodes (2) and (3) to the isolated ground electrode (g) was less than 20 KO then the rat was assigned to the control group. Lower impedances for electrode (1) for the TFS treated group ensured effectiveness of TFS. The skin-to-electrode impedance was rechecked at the end of the experiment.

Next, the tEEG recording and the video recording were started. To evaluate the accuracy of the seizure detection data were collected for each rat in the following way: first, 5 min of baseline tEEG were recorded to train the seizure detector. The seizure detector was activated for 5 min of sham seizure activity (baseline) recording. Finally, seizures were induced with PTZ (55 mg/kg i.p.) and the tEEG recording continued for another 15 min. In the TFS-treated groups one or two doses of TFS were automatically triggered (300 Hz, 50 mA, 200 μs, biphasic square pulses for 2 minutes) and administered between the outer ring and the central disc of electrode (1). Although only two doses were the maximum required to stop the seizures otherwise, more would have been automatically applied if needed. The TFS pulses were generated by a custom-built stimulator that was controlled using a BS2P-24 microcontroller (Parallax Inc., CA, USA).

EXAMPLE 3

Dataset Collection and Analysis

Three seizure detectors were employed (1) supervised CUSUM, and two implementations of GLRT: supervised and unsupervised (further termed (2) sGLRT and (3) uGLRT respectively). For CUSUM and sGLRT we used individualized models of the real-time seizure onset detection i.e. the detector was trained on baseline electrographic activity for each rat. For the uGLRT model there was no training performed on data from individual rats. Detection accuracy was calculated for separate detectors as well as their combination. A disjunctive (logical OR) detector fusion rule was used for detector combination with even a single detection from either one of the three individual detectors occurring more than 15 s after the PTZ injection triggering TFS in real time. The handling period of 15 s was introduced to avoid movement artifacts, caused by handling of the rat related to the PTZ injection, from influencing the seizure onset detection. For the two-dose TFS treated group a 45 s delay in triggering the second TFS dose was introduced after ending the first TFS dose to allow recovery of the amplifiers and assure valid tEEG signals.

All the data collected during the analysis was divided into two datasets. First, the training dataset was collected comprising data from 3 rats, 2 controls and 1 single TFS treated rat. It was used to test the real-time seizure onset detection hardware and software and, more importantly, to determine the suboptimal parameter values for both sGLRT and uGLRT through grid search using the recorded data. The parameter values were selected using a receiver operating characteristic curve based on the tradeoff between maximizing the number of true detections and minimizing the number of false alarms. Suboptimal parameter values for CUSUM were adapted from other work where they were determined using a similar approach. The test dataset consisted of data from a total of 13 rats: 5 controls, 5 rats treated with a single dose of TFS and 3 rats that received two doses of TFS.

CUSUM was applied simultaneously to power in two frequency bands: delta (1-4 Hz) and theta (5-8 Hz). These specific frequency bands were found to yield the highest detection rates in a non-real-time seizure detection model on pre-recorded data. The method first records 5 min of baseline (pre-seizure) activity and the average baseline power $\mu_0$ is calculated for each of the two frequency bands. The baseline activity is divided into non-overlapping segments of data (epochs). A Harming window was applied to each epoch and the power spectrum was calculated using Fast Fourier Transform. For each of the two frequency bands the spectrum was summed over frequencies and normalized by the maximum component. Average power of all the epochs of the baseline activity in each frequency band was used as $\mu_0$.

After that, during sham and real seizure detection epochs were acquired in real time. The same processing method used for baseline was also used to calculate the detection function $g_k$:

$$g_k = \max(g_{k-1} + (x(k) - \mu s - s), 0)$$

where $x(k)$ is the power of the k-th detection epoch and s is a parameter of the CUSUM detector utilized to adjust the detection sensitivity. An epoch was marked as seizure if and only if the value of the detection function was larger than the threshold $\bar{h}$ for both frequency bands. Other suboptimal CUSUM parameter values were employed]. Namely, the size of the decision epoch was equal to 1 s, $\bar{h} = \mu_0$ and $s = 0.1$. Finally, to increase the likelihood that we discriminated seizure from movement artifact we implemented a two-of-three 'seizure' smoothing algorithm for each band. If two out of three consecutive detection epochs were marked by the CUSUM detector as 'seizure' the second 'seizure' was considered as a possible seizure onset. If two of three 'seizure' were detected in both bands then this was the seizure onset. We reasoned that the seizure activity would be prolonged bursts of activity and the movement artifacts would be shorter in duration.

EXAMPLE 3

Mathematical Method for Seizure Detection

A detailed derivation of the properties of GLRT are not covered here. The GLR was applied to verify the change in power between two data segments $x_a(k)$ and $x_b(k)$ ($k=1, \ldots, N$) of equal size N of white Gaussian noise (WGN) with unknown variances $\sigma_a^2$ and $\sigma_b^2$ respectively: $x_a(k) \sim N(0, \sigma_a^2)$ and $x_b(k) \sim N(0, \sigma_b^2)$. An overview of GLRT performance for this case is presented next.

It was determined whether of $\sigma_a^2 < \sigma_b^2$ (due to zero mean the power is equal to the variance) so under the null hypothesis $H_0$: $\sigma_a^2 = \sigma_b^2$ with the alternative being $H_1$: $\sigma_a^2 < \sigma_b^2$. It can be shown that for this case GLRT decides $H_1$ if:

$$T(x) = 2N \ln \frac{\frac{1}{2} \sum_0^{N-1} (x_a^2(k) + x_b^2(k))}{\sqrt{\sum_0^{N-1} x_a^2(k) \sum_0^{N-1} x_b^2(k)}} > \gamma$$

where $T(x)$ is the test statistic and $\gamma$ is the test threshold. From the asymptotic performance of $T(x)\gamma$ can be derived as a function of p value (also called probability of false alarm):

$$\gamma = (Q^{-1}(\tfrac{1}{2}p))^2$$

where $Q^{-1}$ is the inverse of the complementary cumulative distribution function also referred to as the right-tail probability of Gaussian distribution.

sGLRT and uGLRT implementations were used for seizure detection. The main difference was in selection of data segments $x_a$ and $x_b$. For uGLRT, both data segments were taken as non-overlapping segments from the data acquired in real time and were adjacent to each other with $x_a$ immediately preceding $x_b$. In this way the GLRT was detecting a sudden significant increase in power in consecutive segments of data. For sGLRT $x_a$ was selected from baseline tEEG while $x_b$ was taken from sham and real seizure data (data after the PTZ injection) acquired in real time. The following rule was used to select $x_a$: it was selected as one of the non-overlapping baseline segments of size equal to the size of the detection epoch with power closest to the power of the whole baseline segment multiplied by a scaling factor $\alpha > 1$. In this way $x_a$ represents the scaled baseline power while having the size of the detection epoch as required by GLRT. In both cases for each extracted segment the mean was subtracted to comply with the assumption of WGN.

Suboptimal values for GLRT parameters were selected from the training dataset through grid search. A p value equal to 0.05 and 5 sec detection epoch were selected for both sGLRT and uGLRT implementations. The scaling factor $\alpha$ equal to 1.5 was determined for sGLRT in the same way. Finally, to increase the likelihood that we discriminated seizure from movement artifact we implemented a three-of-three 'seizure' smoothing algorithm for both implementations. If three consecutive detection epochs were marked by the sGLRT or uGLRT detectors as seizure the third epoch was considered the seizure onset. Seizure onset detection accuracy was calculated for periods of sham and real seizure until the first observed MJ with the exception of a 30 s handling period centered at the moment of PTZ injection. The first MJ was used as an ending point for seizure onset detection accuracy since it is a clear behavioral manifestation of the seizure activity and for our seizure control we would prefer to detect the seizure before the physical behavioral activity. The actual duration of the seizure segment used to evaluate detection accuracy varied greatly as some rats showed delayed onset of their first MJ until after the recording was finished. In those cases the end of the recording served as the ending of seizure segment for evaluation of detection accuracy. The rats with long latency distorted the average latency of the first MJ for the test dataset (231.8±356.6 s) while the median of 59 s is more accurate.

For each detection method, or a disjunctive combination of methods, the automatically detected seizure score was compared with the gold standard score. For the automatic score each detection epoch was marked as either presence or absence of seizure. For the gold standard every detection epoch belonging to the period starting with the beginning of sham seizure and ending 15 s before the PTZ injection was marked as absence of seizure while every epoch belonging to the period starting 15 s after PTZ injection and ending at the first MJ was marked as seizure.

Since the size of the detection epoch for CUSUM was different from the detection epoch for sGLRT and uGLRT (1 s and 5 s correspondingly) they had to be unified for calculation of seizure detection accuracy. Five second long epochs were used for all three methods with the CUSUM epoch marked as seizure if at least one of 1 s subepochs was marked as seizure by the detector.

The accuracy was calculated by identifying all situations where either automatic or gold standard scores indicated presence of seizure and calculating the numbers of true positives ($T_+$), true negatives ($T_-$), false positives ($F_+$) and false negatives ($F_-$) in terms of 5 s epochs. These detections were later used to calculate sensitivity $$\left(\frac{T_+}{T_+ + F_-}\right)$$

and specificity $$\left(\frac{T_-}{T_- + F_+}\right)$$

to further calculate the overall accuracy $$\left(\frac{T_+ + T_-}{T_+ + T_- + F_+ + F_-}\right)$$

as a weighted average of sensitivity and specificity.

GLRT was used to compare the average power of electrographic seizure activity for the single dose TFS treated and control rats. Since the sizes of data segments $x_a$ and $x_b$ being compared have to be equal for GLRT, the duration of all the segments were set equal to the minimum available data duration from the beginning of the segment to the end of the recording for all the rats. Three and half minutes long segments were selected for each rat starting 4 min after the first valid seizure detection. The 4 min accounted for the duration of TFS for treated rats, full recovery of amplifiers after application of the TFS dose and time needed to turn the TFS on and off.

In a previous study analysis of grand average power spectral densities was performed to compare different stages of seizure development. It showed a significant difference between the TFS treated group and the control group. In the TFS treated group, after TFS, the power spectral density was reduced further towards a pre-seizure "baseline" than it was for the control group. The difference was most obvious in delta (1-4 Hz), theta (5-8 Hz) and alpha (9-13 Hz) frequency bands. Based on these results digital low-pass zero-phase filter (fifth order Butterworth) was applied to data segments $x_a$ and $x_b$ with a cutoff frequency of 15 Hz to emphasize the difference between control and TFS treated groups.

Filtered segments with the mean subtracted were assumed to be WGN with unknown variances. The test hypotheses were defined in the following way: under the null hypothesis powers of two segments corresponding to control ($X_b$) and TFS treated rats ($x_a$) were equal, therefore TFS was not effective in changing the power. The alternative being the power for the segment corresponding to the TFS treated rat is less than the variance for the control rat. The p value was set to 0.001 to ensure significance between the powers from different segments.

EXAMPLE 4

Method for Automated Detection of Seizure Onset

The seizure detection method used normalized tEEG power calculated on per second basis for segments of data from three rats typical for: control (panel A), and one or two doses of TFS treated groups (panels B and C respectively) are presented in FIG. 2. The following parts of the recorded data are presented in the figure for each rat starting from the beginning of the recording: baseline activity (5 min), sham seizure activity (5 min), and real PTZ-induced seizure activity before and after the first MJ. Seizure activity before and after the first MJ are marked differently since the first MJ was used as the end point for seizure onset detection accuracy evaluation. The segments for TFS doses (2 min each) are also marked. The CUSUM, sGLRT and uGLRT individual detections are shown for each rat as well as the valid trigger used to start the TFS dose. For further analysis we refer to the valid trigger detections as seizure onset detections for each detector and the disjunctive combination of detectors.

Average seizure onset detection accuracies, sensitivities and specificities for the test set (n=13) for three separate detectors and their disjunctive combination are presented in Table 1. Since there were limited false positive detections the specificities for all three detectors are high as can be seen in FIG. 2 for the period of sham seizure activity.

TABLE 1

Performance Metrics for CUSUM, sGLRT and uGLRT Detectors.

| Detector | Ave % accuracy | Ave % sensitivity | Ave % specificity | seizure onset prior to the first MJ (%) | Time for detection of seizure onset (s) |
|---|---|---|---|---|---|
| CUSUM | 74.47 | 23.06 | 91.9 | 61.54 | 56 |
| sGLRT | 78.31 | 21.47 | 97.66 | 61.54 | 46 |
| uGLRT | 75.32 | 1.22 | 98.72 | 23.08 | 118 |
| Disjunctive combination | 76.14 | 33.73 | 89.7 | 76.92 | 18 |

The highest average seizure detection accuracy of 7831% was obtained for sGLRT. However, the disjunctive combination of all three detectors gave the highest mean (61.72%) of average sensitivity and average specificity. Specifically there are three other important factors to take into account when evaluating the seizure onset detection performance. First, the percentage of rats in the test group where seizure onset was detected prior to the first MJ. For example, in panel B of FIG. 2 the seizure onset was detected 12 seconds after the first MJ. It can be seen from Table 1 that the highest percentage of 76.92% corresponds to the disjunctive combination of all three detectors. Second, the time between administration of PTZ and detection of seizure onset. From Table 1 the shortest median latency of 18 s corresponds to the disjunctive combination of the three detectors. Finally, the median latency is used in Table 1 instead of mean and standard deviation since the sGLRT, for one of the rats, had no seizure onset detection. Taking all these factors into account we can conclude that the disjunctive combination of all three detectors showed the best performance compared to individual detectors.

FIG. 2 shows that baseline and sham seizure activity segments of the recordings have the least power. After the administration of PTZ there is an increase in electrographic activity in all three rats shown which is expected since PTZ induces high-frequency electrographic spiking activity. After the application of one or two doses of TFS (panels B and C respectively), the power of electrographic seizure activity reduced further towards the baseline. This is in contrast to the control rat (panel A). For conclusive proof that TFS significantly reduced the power of electrographic seizure activity in the TFS treated group compared to controls the GLRT was used on 3.5 min long segments of data. Data from a total of 5 TFS treated rats (single TFS dose) and 4 controls from the test set were used. The electrode interface cable of the fifth control rat of the test set was disconnected by severe movements during PTZ-induced clonic activity with rearing and falling. Therefore, the data from the fifth control rat had to be excluded from this part of the study. The GLRT was applied to pairs of data segments corresponding to control and single dose TFS treated groups and the results were averaged for all the pairs. The GLRT showed that TFS significantly (p=0.001) reduced the power of the electrographic seizure activity in the single dose TFS treated group compared to controls in 70% of the pairs. The median power for the TFS group was 2.2 times smaller than the median power for the control group with average standard errors in both groups being below 8% and 3% of the median power respectively.

EXAMPLE 5

Method for Automated Detection of Seizure Onset

From Table 1 it can be seen that out of three proposed detectors the worst performance was from the uGLRT. This is to be expected since it was the only unsupervised detector. Our motivation to include it into this study was an important advantage of unsupervised detectors—they can be applied to the data from a rat the detector has never been trained on.

The performance of the two supervised detectors, CUSUM and sGLRT, was comparable in terms of all the performance metrics. The sGLRT performed slightly better especially on sham seizure (specificity of 97.66% compared with 91.9% for CUSUM) as can be seen, for example, in panel C of FIG. 2. This is important since in real life applications a false positive detection may mean an extra dose of electrical stimulation or a dose of anticonvulsant drug. As a result of a tradeoff higher specificities mean lower sensitivities but even with the sensitivity of 33.73% for a disjunctive combination of all three detectors the seizure onset was detected prior to the first MJ in 76.92% of rats of the test set (n=13). At the same time disadvantages of sGLRT compared to CUSUM include a much larger detection epoch (5 s compared with 1 s for CUSUM) and the fact that it was the only detector that failed to detect seizure onset in one of the rats completely.

Since all of the proposed detectors are detecting an increase in tEEG power the strong movement artifacts pose a risk of causing false positive detections. One example of such an artifact that was observed to cause false positive detections during the data collection was when a rat was grooming with the paws touching the head electrode cap and connector cables. Artifacts occurring during the baseline part of the recording also pose a threat as the performance of supervised seizure detectors such as CUSUM and sGLRT rely on baseline power of a particular rat. Higher power of the baseline signal due to multiple artifacts increases the detection threshold causing false negative detections and therefore lowering the sensitivity.

Another important consideration is the second TFS trigger seizure detection in the two dose TFS treated group. For the first valid seizure onset detection in rats of the test set, in most cases (76.92% for a disjunctive combination of three detectors), detections occurred before the first MJ. According to a widely used scoring scheme for seizure-related behavioral activity the first MJ is the first strong behavioral seizure manifestation. There may be other behavioral activity, which include only oral-facial movements and head nodding. After the first MJ, as the seizure develops, the amount of movement artifacts is likely to increase as rats may pass through a number of stages including multiple MJs, forelimb clonus, and severe clonic activity with rearing and falling and wild running fit. Depending on the maximum seizure stage for a particular rat the amount of movement artifacts affecting the second seizure detection may differ. Further investigation is needed to assess the percentage of second seizure detections based on tEEG power that may be attributed to movement artifacts rather than seizure-related brain activity.

Results obtained for assessment of effect of TFS on power of the electrographic seizure activity using GLRT in this study are worse than the ones obtained in previous ones. In this study the application of GLRT showed that TFS significantly (p=0.001) reduced the power of the electrographic PTZ-induced seizure activity in the single TFS treated group (n=5) compared to controls (n=4) in 70% of the compared segments while in some cases significant (p=0.001) reduction in the TFS treated group (n=6) compared to controls (n=5) occurred in more than 86% of the pairs. The major difference between these two studies is that in the current study TFS was triggered automatically while in the other it had to be turned on manually after the first MJ was observed.

An important limitation is the GLRT requirement of equal sizes of data segments to compare. In the current study, the selection of data segments was kept consistent for control and TFS treated groups. Such time-synchronized data segmentation allows us to directly compare between corresponding groups. However, electrographic activity caused by PTZ-induced seizures is non-stationary and highly variable with periods of intense spiking activity interchanging with periods of very low activity intensities. Strict guidelines for data segment selection make the analysis vulnerable to selection partially or fully during calm periods which are less representative of the induced seizure activity.

In FIG. 2 the power of seizure electrographic activity was reduced the furthest towards the pre-seizure baseline for the two dose TFS treated rat with no more seizure detections after the second dose of TFS (FIG. 2, panel C). Seizure electrographic activity for the single dose TFS treated rat also reduced towards baseline after the single dose of TFS but not as drastically as in the two dose TFS administration (FIG. 2, panel B). Not surprisingly, the power of the seizure electrographic activity for the control rat stays high due to the continuing effect of PTZ with multiple seizure detections (FIG. 2, panel A).

Automatic seizure detection methodology based on a disjunctive combination of CUSUM and GLRT was validated on both sham and PTZ induced seizures in rats. These seizure detectors were part of an automated feedback seizure control system based on single or double doses of TFS administered via TCRE, however more than two could be administered if required to control a seizure. An average seizure onset detection accuracy of 76.14% with sensitivity of 33.73% and specificity of 89.7% was obtained for the test set (n=13). Detection of electrographic seizure activity was accomplished in advance of the early behavioral seizure activity in 76.92% of the cases. Automatically triggered TFS significantly (p=0.001) reduced the electrographic seizure activity power in the single dose TFS treated group (n=5) compared to controls (n=4) in 70% of the paired segments further suggesting its anticonvulsant effect. These results demonstrate the potential of an automatic seizure control system using TCRE electrographic seizure activity as feedback.

EXAMPLE 6

Neurotransmitter Modulation of γ-Aminobutyric Acid (GABA) and Glutamate by Transcranial Focal Stimulation The ability of TFS to affect epilepsy suggested that TFS may impact specific neurotransmitters of the brain itself. To evaluate whether TFS could alter brain signaling modulation, a similar procedure was performed as described by Luna-Munguia but substituting TFS for 130 Hz deep brain stimulation in the hippocampus. Microdialysis and high performance liquid chromatography (HPLC) fluorometric detection was used to quantify specific neurotransmitters.

Prior to the study, bipolar electrodes, consisting of two twisted strands of stainless steel wire, insulated except at the cross-section of their tips, were stereotactically implanted into the left ventral hippocampus. A microdialysis guide cannula was attached to the bipolar electrode. Stainless steel screws were threaded into the cranium over the frontal cortex to fix the electrode assembly. A 6.0 mm diameter TCRE was centered on the top of the skull with the front ring caudal to the bregma. The bipolar electrode was just beyond the perimeter of the TCRE with the bare conductors inside the hippocampus. The electrodes assembly was fixed to the skull with dental acrylic.

A continuously perfused dialysis probe was inserted into the guide cannula and anchored with dental acrylic. TFS, applied via the 6.0 mm diameter TCRE on the skull, was delivered at 300 Hz with 200 μS biphasic pulses starting at 100 μA and gradually increased by 20% at a time. The TFS application was discontinued when motor behaviors occurred (threshold current) during short (15 s) stimulation trains with 2 min pauses. On the following day background neurotransmitter levels were measured at a 20% subthreshold current, which was applied for 20 or 30 minutes. Dialysate samples were continued for 1.5 hours after the TFS to determine if there were any lasting effects on the neurotransmitters.

In FIGS. 3A-3B, it is demonstrated for the first time that TFS caused modulation of neurotransmitters. It was found that two known neurotransmitters, GABA and glutamate, were elevated and decreased in the hippocampus after TFS stimulation was discontinued, respectively. The coordinated modulation of the two neurotransmitters provides a novel approach to control epilepsy in a closed loop manner using detection and stimulation with monitoring of neurotransmitters. In particular glutamate is considered an excitatory neurotransmitter and as shown in FIGS. 3A-3B TFS significantly decreased glutamate. Also, in FIGS. 3A-3B it can be observed that GABA was significantly increased and is considered an inhibitory neurotransmitter. The enhancement of inhibition is compounded by lessening of the excitatory ability.

In TFS group, extracellular amino acid levels under basal conditions were similar to those obtained from the control group. When TFS was applied, high extracellular levels of GABA and low extracellular levels of glutamate were detected during and after the stimulation as follows. GABA in the third (20-30 minutes after stimulation started) and eighth (85-100 minutes after stimulation started) dialysate collected (570%, $p<0.05$ and 116%, $p<0.05$, respectively); while glutamate in the fifth (40-55 minutes after stimulation started) and the tenth (115-130 minutes after stimulation started) dialysate collected (51%, $p<0.01$ and 31%, $p<0.05$, respectively). Although GABA and glutamate values remained elevated or diminished, respectively, since the third and the fifth dialysate collections after TFS started, only the significant differences previously mentioned were observed.

These results demonstrate for the first time that TFS is effective in modulating levels of neurotransmitters within the brain from outside the brain. Together with previous results disclosed herein, TFS is shown for the first time to be effective in controlling and modulating neurotransmitters and drugs to improve neurological brain injuries, brain dependency, and brain diseases such as epilepsy.

EXAMPLE 7

Transcranial Focal Stimulation Improves Anti-Epileptic Sub-Effective Drug Potency Epilepsy is characterized by recurrent, spontaneous, and unpredictable seizures that have been associated with a chemical imbalance between excitatory and inhibitory neurotransmitters. Clinical studies indicate that pharmacoresistant temporal lobe epilepsy (TLE) is related to a failure of neurotransmission mediated by glutamate and T-aminobutyric acid (GABA).

This study was designed to evaluate status epilepticus (SE) induced by lithium-pilocarpine (LP) in rats receiving TFS, alone and combined with subeffective doses of diazepam, an antiepileptic drug that belongs to the group of benzodiazepines. Diazepam is currently considered one of the drugs of choice to stop SE.

Nearly all the animals from the LP group (96%) showed generalized seizures and SE. Latencies to behavioral changes evaluated after pilocarpine administration were as follows: first forelimb clonus at 23.9±1.6 min; first generalized seizure at 25.6±1.6 min; and establishment of SE at 30.3±1.6 min.

Non-significant changes were found in latency and incidence of LP-induced behavioral alterations when subeffective doses of diazepam were administered prior to the pilocarpine, in comparison to the LP group. All rats presented seizures and SE.

When compared with the LP group, the LP+TFS group showed a lower percentage of animals reaching SE (71%, $p<0.05$). The incidence of forelimb clonus, generalized seizures, as well as the latency to the first forelimb clonus, generalized seizure, and establishment of SE were not significantly different. A total protection against LP-induced seizures was produced in 21% of the rats.

The administration of a subeffective dose of diazepam combined with TFS produced a total protection against LP-induced seizures and SE in 62% of the animals, and was significantly different when compared with the LP and LP+DZP groups (p<0.0001 and p<0.003, respectively). The LP+TFS+DZP group also had a significantly increased latency to the first forelimb clonus (p<0.001), mild generalized seizure (p<0.001), and the establishment of the SE (p<0.001), when compared with LP, LP+DZP, and LP+TFS groups.

During and after the TFS, animals did not show behavioral changes. Surprisingly, the data obtained from this study reveals that a subeffective dose of diazepam improves the anticonvulsant effects induced by TFS in LP-induced SE.

The reduced incidence of severe generalized seizures in animals receiving TFS during the LP-induced SE is possibly due to mechanisms involving the activation of GABAergic terminals and subsequent GABA release as well as the depression of subliminal voltage-gated currents underlying spontaneous spikes. It was found that TFS combined with a subeffective dose of diazepam enhanced the latency to LP-induced seizures. Diazepam, as a benzodiazepine agonist, increases the channel opening frequency in the presence of GABA, increasing the effects of this amino acid. The augmented release of GABA in the hippocampus of normal rats following TFS support the idea that release of neurotransmitters and activation of $GABA_A$ receptors play an important role in the HFS-induced effects. This is evidenced by the persistent enhanced release of GABA detected in the TFS-treated rats 100 minutes after TFS ceased (FIGS. 3A-3B) that was similar to that found in the hippocampus and substantia nigra pars compacta of normal rats receiving DBS directly in the hippocampus. On the other hand, TFS in normal rats did not increase glutamate extracellular levels in contrast with the DBS-induced transient hippocampal release of this amino acid in normal animals.

It has been shown that deep brain stimulation (DBS) modulated neurotransmitters (in particular increasing GABA) and was not detrimental to memory. Also, it has been shown that DBS had an enhancing effect on diazepam, and other antiepileptic drugs or AEDs. From these previous results TFS was expected to have similar effects on GABA and since diazepam enhances GABA activity diazepam was our first choice to test. These results went beyond expectation fully protecting 62 percent of the rats that received the combination of LP+TFS+DZP. For the first time, the present invention showed that there were dramatic anticonvulsant enhancement properties of sub-effective doses of diazepam in conjunction with TFS. This was surprising since TFS is a non-invasive method to enhance sub-effective drug potency or significantly reduce levels of anti-epileptic drugs that have negative side effects at higher doses.

The results obtained from the present study support the potential that TFS applied in an epileptogenic brain area is safe and effective for controlling acute seizure and possibly drug resistant epilepsy. Further, it is demonstrated that TFS is more effective in the presence of enhanced GABAergic neurotransmission.

EXAMPLE 8

Non-Invasive Method to Detect Neurotransmitters Levels Impacted by Transcranial Focal Stimulation It was previously described how one can quantify neurotransmitter changes with respect to minimally invasive TFS applied on the skull. In accordance with certain this invention, TFS could be applied noninvasively and neurotransmitters are measured using a more preferred method of neurotransmitter sensing using nuclear magnetic resonance (NMR). Pan et al. found a relationship that a lower ratio of phosphocreatine/adenosine triphosphate (PCr/ATP) is linked with higher concentrations of glutamate as measured in the ipsilateral hippocampus of mesial TLE patients. Using the NMR one is able to noninvasively measure analytes that correlate with concentrations of glutamate. Glutamate is considered excitatory and a cause of seizures. Therefore, by applying noninvasive TFS and noninvasively imaging with NMR to correlate changes in PCr/ATP, a high degree of confidence is related that TFS is lowering glutamate.

In this new aspect of the invention, the tripolar concentric ring electrode can be placed on the scalp, preferably with some form of impedance matching, and then TFS can be applied using 300 Hz, 200 μs biphasic, equal charge, square pulses, or other appropriate TFS parameters. The use of NMR is slow like using microdialysis. Using the FSCV or fast amperometry (a similar electrochemistry method) it is possible to acquire second-by-second neurotransmitter feedback to guide the application of TFS. The neurotransmitter sensing electrodes could be used in conjunction with wireless transmission providing feedback for the noninvasive TFS. In this way, the application of TFS is performed in a much more targeted method by the stimulation for shorter periods of time and assessing that the neurotransmitters are being modulated in the appropriate direction. It is expected that once the patient has undergone analysis of neurotransmitter levels then a routine interaction protocol is designed to be patient specific.

Those skilled in the art will appreciate that numerous modifications and variations may be made to the above disclosed embodiments without departing from the spirit and scope of the present invention.

What is claimed is:

1. A method for controlling electrical activity in a target area of the body using a transcranial focal stimulation, said method comprising the steps of:
   a. recording an animal electrical activity in a target area of the body using a concentric ring electrode used in an electroencephalography device;
   b. analyzing concentric ring electrode electroencephalography output for electrical activity in the target area by a cumulative sum algorithm or a generalized likelihood ratio or combination thereof;
   c. detecting said electrical activity in the target area that is not within range;
   d. triggering transcranial focal stimulation applied via the concentric ring electrode to alter said electrical activity in a target area of the body; and
   e. continuing said transcranial focal stimulation until said electrical activity level in the target area is controlled.

2. The method of claim 1, wherein said concentric ring electrode used in the electroencephalography device is a tripolar concentric ring electrode.

3. The method of claim 1, wherein said concentric ring electrode includes at least two concentric rings.

4. The method of claim 1, wherein said method improves efficacy of a drug.

5. The method of claim 1, wherein said method differentially stimulates production of one of γ-aminobutyric acid (GABA) and glutamate, but not both GABA and glutamate.

6. The method of claim 1 for controlling the electrical activity in a target area of the body, wherein the target area of the body is the brain.

7. A method for controlling the electrical activity in a target area of the body using a transcranial focal stimulation and using a drug, said method comprising the steps of:
   a. recording an animal electrical activity in a target area of the body using a concentric ring electrode used in an electroencephalography device;
   b. analyzing concentric ring electrode electroencephalography output for electrical activity in the target area by a cumulative sum algorithm or a generalized likelihood ratio or combination thereof;
   c. detecting when said electrical activity in the target area is not within range;
   d. administering the drug to adjust the electrical activity of the target area to the normal range;
   e. administering the transcranial focal stimulation to adjust the electrical activity of the target area to the normal range; and
   f. repeating said administration of said drug or continuing said transcranial focal stimulation to control said electrical activity level to the normal range in the target area.

8. The method of claim 1 or 7 for controlling the electrical activity in a target area of the body, wherein said target area of the body is the brain, heart, or muscle.

9. The method of claim 7, wherein said concentric ring electrode used in the electroencephalography device is a tripolar concentric ring electrode.

10. The method of claim 7 for controlling the electrical activity in a target area of the body, wherein said target area is the brain.

11. The method of claim 7, wherein said concentric ring electrode includes at least two concentric rings.

12. The method of claim 7, wherein said method improves efficacy of the drug.

13. The method of claim 12, wherein said method improves efficacy of the drug by reducing the dosage necessary for effect of the drug.

14. The method of claim 12, wherein said method improves efficacy of the drug by increasing the potency of the drug.

15. The method of claim 7, wherein said method differentially stimulates production of one of γ-aminobutyric acid (GABA) and glutamate, but not both GABA and glutamate.

16. A method for controlling an epileptic seizure in the brain using an automated seizure control system, comprising:
   a. detecting whether the epileptic seizure event that exceeds a pre-set seizure activity;
   b. analyzing electroencephalography output for the epileptic seizure event by a cumulative sum algorithm or a generalized likelihood ratio or combination thereof and monitoring levels of neurotransmitter in the brain;
   c. triggering transcranial focal stimulation using a concentric ring electrode in response to the epileptic seizure event;
   d. triggering a release of a drug in response to the epileptic seizure event; and
   e. continuing at least one of steps c and d until the epileptic seizure has stopped or neurotransmitter level returns to the normal level.

17. The method of claim 16, wherein said concentric ring electrode is a tripolar concentric ring electrode.

18. The method of claim 16, wherein the method improves efficacy of the drug.

19. The method of claim 18, wherein said method improves efficacy of the drug by reducing the dosage necessary for effect of the drug.

20. The method of claim 18, wherein said method improves efficacy of the drug by increasing the potency of the drug.

21. The method of claim 16, wherein said concentric ring electrode includes at least two concentric rings.

22. The method of claim 16, wherein said method differentially stimulates production of one of γ-aminobutyric acid (GABA) and glutamate, but not both GABA and glutamate.

23. A method for the automated control of an epileptic seizure event, comprising:
   a. recording an animal brain activity using an electroencephalography device;
   b. analyzing electroencephalography output for the epileptic seizure event by a cumulative sum algorithm or a generalized likelihood ratio or combination thereof;
   c. detecting of the epileptic seizure event that exceeds a pre-set seizure activity;
   d. triggering transcranial focal stimulation applied using a concentric ring electrode in response to the epileptic seizure event;
   e. triggering release of a drug in response to the epileptic seizure event; and
   f. continuing at least one of steps d and e until the epileptic seizure event has stopped.

24. The method of claim 23, wherein said concentric ring electrode is a tripolar concentric ring electrode.

25. The method of claim 23, wherein the method improves efficacy of the drug.

26. The method of claim 25, wherein said method improves efficacy of the drug by reducing the dosage necessary for effect of the drug.

27. The method of claim 25, wherein said method improves efficacy of the drug by increasing the potency of the drug.

28. The method of claim 23, wherein said concentric ring electrode includes at least two concentric rings.

29. The method of claim 23, wherein said method differentially stimulates production of one of γ-aminobutyric acid (GABA) and glutamate, but not both GABA and glutamate.

30. A method for controlling electrical activity in a target area of the body using a transcranial focal stimulation, said method comprising the steps of:
   recording an animal electrical activity in a target area of the body using a concentric ring electrode used in an electroencephalography device;
   analyzing concentric ring electrode electroencephalography output for electrical activity in the target area by a cumulative sum or a generalized likelihood ratio or combination thereof;
   detecting said electrical activity in the target area that is not within range;
   triggering transcranial focal stimulation applied via the concentric ring electrode to alter said electrical activity in a target area of the body; and
   continuing said transcranial focal stimulation until said electrical activity level in the target area is controlled.

31. The method of claim 30 for controlling the electrical activity in a target area of the body, wherein said target area of the body is the brain, heart, or a muscle.

32. The method of claim 30, wherein said concentric ring electrode used in the electroencephalography device is a tripolar concentric ring electrode.

33. The method of claim 30 for controlling the electrical activity in a target area of the body, wherein said target area of the body is the brain.

34. The method of claim 30, wherein said concentric ring electrode includes at least two concentric rings.

35. The method of claim 30, wherein said method improves efficacy of a drug.

36. The method of claim 30, wherein said method differentially stimulates production of one of γ-aminobutyric acid (GABA) and glutamate, but not both GABA and glutamate.

37. A method for controlling an epileptic seizure in the brain using an automated seizure control system, comprising:
   detecting whether the epileptic seizure event exceeds a pre-set seizure activity;
   analyzing electroencephalography output for the epileptic seizure activity by a cumulative sum algorithm or a generalized likelihood ratio or a combination thereof and monitoring levels of neurotransmitter in the brain;
   triggering transcranial focal stimulation using a concentric ring electrode in response to the epileptic seizure event; and
   continuing stimulation until the epileptic seizure has stopped or neurotransmitter level returns to the normal level.

38. The method of claim 37, wherein said concentric ring electrode is a tripolar concentric ring electrode.

39. The method of claim 37, wherein said concentric ring electrode includes at least two concentric rings.

40. The method of claim 37, wherein said method differentially stimulates production of one of γ-aminobutyric acid (GABA) and glutamate, but not both GABA and glutamate.

41. The method of claim 38, wherein the method improves efficacy of a drug.

42. A method for controlling an epileptic seizure event in the brain using an automated seizure control system, comprising:
   detecting whether neurotransmitter level exceed a pre-set seizure activity;
   analyzing electroencephalography output for the epileptic seizure event by a cumulative sum algorithm or a generalized likelihood ratio or combination thereof and monitoring levels of neurotransmitter in the brain;
   triggering transcranial focal stimulation using a concentric ring electrode in response to the epileptic seizure event; and
   continuing stimulation until neurotransmitter level returns to a normal level not exceeding the pre-set seizure activity.

43. The method of claim 42, wherein said concentric ring electrode includes at least two concentric rings.

44. The method of claim 42, wherein said concentric ring electrode is a tripolar concentric ring electrode.

45. The method of claim 42 further comprising administrating a drug, wherein said method improves efficacy of the drug.

46. The method of claim 42, wherein said method differentially stimulates production of one of γ-aminobutyric acid (GABA) and glutamate, but not both GABA and glutamate.

47. A method for controlling an electrical activity in a target area of the body using a transcranial focal stimulation, said method comprising the steps of:
   a. recording an animal electrical activity in a target area of the body using a concentric ring electrode used in an electroencephalography device;
   b. analyzing concentric ring electrode electroencephalography output for electrical activity in the target area by at least one of a cumulative sum algorithm and a generalized likelihood ratio;
   c. detecting said electrical activity in the target area that is not within range;
   d. triggering transcranial focal stimulation applied via the concentric ring electrode in response to a specified electrical activity;
   e. releasing of a drug in response to the specified electrical activity; and
   e. continuing at least one of steps (d) and (e) until said electrical activity level in the target area is controlled.

48. The method of claim 47, wherein said concentric ring electrode includes at least two concentric rings.

49. The method of claim 47, wherein said concentric ring electrode is a tripolar concentric ring electrode.

50. The method of claim 47, wherein the target area of the body is the brain.

51. The method of claim 47, wherein said method improves efficacy of the drug.

52. The method of claim 47, wherein said method differentially stimulates production of one of γ-aminobutyric acid (GABA) and glutamate, but not both GABA and glutamate.

* * * * *